US007635674B2

United States Patent
Szilvássy et al.

(10) Patent No.: US 7,635,674 B2
(45) Date of Patent: Dec. 22, 2009

(54) SYNERGISTIC PHARMACEUTICAL COMBINATION FOR THE PREVENTION OR TREATMENT OF DIABETES

(75) Inventors: Zoltán Szilvássy, Debrecen (HU); György Rabloczky, Budapest (HU); András Rabloczky, legal representative, Budapest (HU); Péter Literáti Nagy, Budapest (HU)

(73) Assignee: N-Gene Research Laboratories, Inc., New York, NY (US)

( * ) Notice: Subject to any disclaimer, the term of this patent is extended or adjusted under 35 U.S.C. 154(b) by 795 days.

(21) Appl. No.: 10/495,240

(22) PCT Filed: Jul. 10, 2002

(86) PCT No.: PCT/HU02/00067

§ 371 (c)(1),
(2), (4) Date: Feb. 11, 2005

(87) PCT Pub. No.: WO03/007951

PCT Pub. Date: Jan. 30, 2003

(65) Prior Publication Data

US 2007/0015687 A1 Jan. 18, 2007

(30) Foreign Application Priority Data

Jul. 17, 2001 (HU) .................... 0102982
Jul. 5, 2002 (HU) .................... 0202204

(51) Int. Cl.
*A61K 38/28* (2006.01)
(52) U.S. Cl. ....................................................... 514/4
(58) Field of Classification Search ................. None
See application file for complete search history.

(56) References Cited

U.S. PATENT DOCUMENTS

| 4,308,399 | A |   | 12/1981 | Takacs et al. |
|-----------|---|---|---------|---------------|
| 5,190,970 | A | * | 3/1993  | Pan et al. .................... 514/423 |
| 5,328,906 | A | * | 7/1994  | Nagy et al. ............... 514/235.5 |
| 6,011,049 | A | * | 1/2000  | Whitcomb .................. 514/369 |
| 6,121,278 | A | * | 9/2000  | Jackson et al. .............. 514/292 |
| 6,153,632 | A | * | 11/2000 | Rieveley .................... 514/369 |
| 6,291,495 | B1| * | 9/2001  | Rieveley .................... 514/369 |

FOREIGN PATENT DOCUMENTS

| WO | WO 00/07580  | * | 2/2000 |
| WO | WO 00 07580 A |   | 2/2000 |
| WO | WO 00/14054  | * | 3/2000 |
| WO | WO 00 14054 A |   | 3/2000 |

OTHER PUBLICATIONS

American Diabetes Association "Management of dyslipidemia in adults with diabetes" Diabetes Care, 2003, 26, 83-S86.*
Mayo Clinic (http://www.mayoclinic.com/print/hair-loss/DS00278).*
Mayo Clinic (http://www.mayoclinic.org/metabolic-disorders/treatment.html).*
Klein et al., "Serum cholesterol in Wisconsin epidemiologic study of diabetic retinopathy," Diabetes Care, 1992, 15, 282-287.*

* cited by examiner

*Primary Examiner*—Cecilia Tsang
*Assistant Examiner*—Christina Bradley
(74) *Attorney, Agent, or Firm*—Birch, Stewart, Kolasch & Birch LLP

(57) ABSTRACT

The invention refers to a synergistic pharmaceutical combination which comprises (a) a first pharmaceutical composition containing an antidiabetic or anti-hyperlipidemic active agent and one or more conventional carrier(s), and (b) a second pharmaceutical composition containing a hydroximic acid derivative of the formula I and one or more conventional carrier(s). The pharmaceutical combination is suitable for the prevention or treatment of, among others, diabetes mellitus.

4 Claims, No Drawings

US 7,635,674 B2

SYNERGISTIC PHARMACEUTICAL COMBINATION FOR THE PREVENTION OR TREATMENT OF DIABETES

The invention refers to a synergistic pharmaceutical combination suitable for the prevention or treatment of a prediabetic state, metabolic X-syndrome or diabetes mellitus as well as disorders which are associated with the states listed above, namely endogenic metabolic disorders, insulin resistance, dislipidemia, alopecia, diffuse effluvium and/or female endocrinic disorders based on androgenic preponderance.

In the industrially developed countries more and more human being suffers from diabetes. For example, the development of type 2 diabetes (i.e. non-insulin-dependent diabetes mellitus, NIDDM) is promoted by the defects in both the production and use of insulin. Genetic and environmental factors equally contribute to the formation of this wide-spread serious disease accompanied by significant mortality. The patient treated with insulin or another antidiabetic or anti-hyperlipidemic agent obtains, as a matter of fact, only a palliative treatment that improves the life quality, however, the complications which accompany the diabetes appear unavoidably.

The aim of the invention is to provide a pharmaceutical combination which is suitable for the prevention of the development of diabetes or at least the complications that accompany diabetes, or, if such prevention is not possible anymore, for the efficient treatment of said complications.

It was found that the above aim is achieved by a synergistic pharmaceutical combination comprising (a) a first pharmaceutical composition containing an antidiabetic or anti-hyperlipidemic active agent and one or more conventional carrier(s), and (b) a second pharmaceutical composition containing a hydroximic acid derivative of the formula

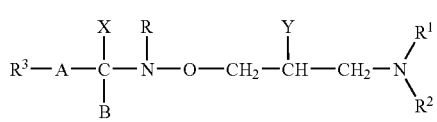
I wherein
$R^1$ represents a hydrogen atom or a $C_{1-5}$ alkyl group,
$R^2$ stands for a hydrogen atom, a $C_{1-5}$ alkyl group, a $C_{3-8}$ cycloalkyl group or a phenyl group optionally substituted by a hydroxy or a phenyl group, or
$R^1$ and $R^2$ together with the nitrogen atom they are attached to form a 5- to 8-membered ring optionally containing one or more further nitrogen, oxygen or sulfur atom(s) and said ring can be condensed with another alicyclic or heterocyclic ring, preferably a benzene, naphthalene, quinoline, isoquinoline, pyridine or pyrazoline ring, furthermore optionally the nitrogen and/or sulfur heteroatom(s) is/are present in the form of an oxide or dioxide,
$R^3$ means a hydrogen atom, a phenyl group, a naphthyl group or a pyridyl group wherein said groups can be substituted by one or more halo atom(s) or $C_{1-4}$ alkoxy group(s),
Y is a hydrogen atom, a hydroxy group, a $C_{1-24}$ alkoxy group optionally substituted by an amino group, a $C_{2-24}$ polyalkenyloxy group containing 1 to 6 double bond(s), a $C_{1-25}$ alkanoyl group, a $C_{3-9}$ alkenoyl group or a group of the formula $R^7$—COO— wherein $R^7$ represents a $C_{2-30}$ polyalkenyl group containing 1 to 6 double bond(s),
X stands for a halo atom, an amino group, a $C_{1-4}$ alkoxy group or
X forms with B an oxygen atom, or
X and Y together with the carbon atom they are attached to and the —NR—O—CH$_2$— group being between said carbon atoms form a ring of the formula

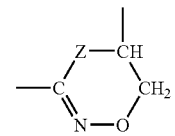
a wherein
Z represents an oxygen atom or a group of the formula —N═ or —NH—,
R stands for a hydrogen atom or
R forms with B a chemical bond,
A is a $C_{1-4}$ alkylene group or a chemical bond or a group of the formula

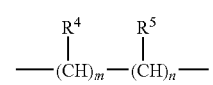
b wherein
$R^4$ represents a hydrogen atom, a $C_{1-5}$ alkyl group, a $C_{3-8}$ cycloalkyl group or a phenyl group optionally substituted by a halo atom, a $C_{1-4}$ alkoxy group or a $C_{1-5}$ alkyl group,
$R^5$ stands for a hydrogen atom, a $C_{1-4}$ alkyl group or a phenyl group,
m has a value of 0, 1 or 2,
n has a value of 0, 1 or 2, or a pharmaceutically suitable acid addition salt thereof, and one or more conventional carrier(s).

The invention is based on the recognition that the hydroximic acid derivatives of the formula I enhance the sensitivity of insulin. Therefore, in the presence of a hydroximic acid derivative of the formula I or a pharmaceutically suitable acid addition salt thereof, the antidiabetic or anti-hyperlipidemic active agent employed for the treatment of the pathological state can be administered in a significantly lower dosage to achieve the aimed effect, thereby reducing or eliminating the side-effects that accompany the traditional treatment.

The hydroximic acid derivatives of the formula I are known from U.S. Pat. No. 4,308,399 and EP No. 417 210. According to these documents, the compounds can be employed for the treatment of diabetic angiopathy, and a part of them has selective beta-blocking effect.

According to Hungarian patent application No. 2385/92 published under No. T/66350, certain hydroximic acid derivatives within the formula I can be used in the treatment of vascular complications due to diabetes.

Various further biological effects of the hydroximic acid derivatives of the formula I are also known, among others the use thereof for the prevention and treatment of diseases of mitochondrial origin (WO 97/13504), for enhancing the stress protein level of cells (WO 97/16439), for delaying the aging processes of skin (WO 97/23198), against autoimmune diseases (WO 00/07580) etc.

DEFINITION OF EXPRESSIONS USED IN THE DESCRIPTION AND CLAIMS

A pharmaceutical combination is an association of two pharmaceutically active agents in which
1) either each of the active agents has been converted, one by one, to separate pharmaceutical compositions using one or more conventional carrier(s) and any of the usual processes of drug manufacture, and in this case the two sorts of pharmaceutical composition obtained are administered to the patient simultaneously or one after the other following an interval;
2) or the two active agents have been converted to one single pharmaceutical composition that can be administered to the patient being in need thereof. In the latter case, the pharmaceutical composition may contain a mixture of the two active agents, or each of the active agents may be present at a different site in the pharmaceutical composition, e.g. one of them in the tablet core and the other in a coating of the tablet core. Of course, one or more conventional carriers and any of the usual processes of drug manufacture are used to prepare this single pharmaceutical composition.

Under an antidiabetic active agent any of the pharmacologically active agents conventionally used in the therapy for the treatment of diabetes is meant. These are mainly the following:
insulin,
insulin sensitizing active agents,
active agents that enhance the production of insulin,
sulfonamides,
biguanidine derivatives and
α-glucosidase inhibitors.

As insulin, in the first place, human insulin prepared by recombinant technology is employed, which is administered, in general, parenterally.

The insulin sensitizing active agents enhance the effect of insulin. The most important sorts of them are the PPAR (peroxisome proliferator-activated receptor) γ-agonists, for example the thiazolidinedione derivatives such as pioglitazone [(±)-5-[[4-[2-(5-ethyl-2-pyridinyl)ethoxy]phenyl]methyl]-2,4-thiazolidinedione], troglitazone [(±)-5-[[4-[(3,4-dihydro-6-hydroxy-2,5,7,8-tetramethyl-2H-1-benzopyran-2-yl)methoxy]-phenyl]methyl]-2,4-thiazolidinedione], ciglitazone [5-[[4-[(1-methylcyclohexyl)methoxy]phenyl]methyl]-2,4-thiazolidine-dione, rosiglitazone [(±)-5-[4-[2-[N-methyl-N-(2-pyridyl)amino]-ethoxy]benzyl]-2,4-thiazolidinedione] and other 2,4-thiazolidinedione derivatives as well as pharmaceutically suitable acid addition salts thereof.

The active agents that enhance the production of insulin are, for example, as follows: mitiglinide [(αS,3aR,7aS) -octahydro-γ-oxo-α-(phenylmethyl)-2H-isoindole-2-butanoic acid], repaglinide [(S)-2-ethoxy-4-[2-[[3-methyl-1-[2-(1-piperidinyl)phenyl]butyl]amino]-2-oxoethyl]benzoic acid], senaglinide (i.e. nateglinide) [N-[[(trans-4-(1-methylethyl) -cyclohexyl]carbonyl]-D-phenylalanine] or pharmaceutically suitable acid addition salts or pharmaceutically suitable salts thereof.

Out of the sulfonamides, the most important ones are the sulfonylurea derivatives e.g. tolbutamide [N-[(butylamino)-carbonyl]-4-methylbenzenesulfonamide], chlorpropamide [4-chloro-N-[(propylamino)carbonyl]benzenesulfonamide], tolazamide [N-[[(hexahydro-1H-azepin-1-yl)amino]carbonyl]-4-methylbenzenesulfonamide], acetohexamide [4-acetyl-N-[(cyclohexylamino)carbonyl]benzenesulfonamide] etc. as first generation sulfonylureas or, for example, glyburide [5-chloro-N-[2-[4-[[[(cyclohexylamino)carbonyl]amino]sulfonyl]phenyl]-ethyl]-2-methoxybenzamide], glipizide [N-[2-[4-[[[(cyclohexyl-amino)carbonyl]amino]sulfonyl]phenyl]ethyl]-5-methylpyrazine-carboxamide], gliclazide [N-[[(hexahydrocyclopenta[c]pyrrol-2(1H)-yl) amino]carbonyl]-4-methylbenzenesulfonamide], glimepiride [trans-3-ethyl-2,5-dihydro-4-methyl-N-[2-[4-[[[[(4-methylcyclohexyl)amino]carbonyl]amino]sulfonyl]phenyl] ethyl]-2-oxo-1H-pyrrole-1-carboxamide], gliquidone [N-[(cyclohexyl-amino)carbonyl]-4-[2-(3,4-dihydro-7-methoxy-4,4-dimethyl-1,3-dioxo-2(1H)-isoquinolinyl) ethyl]benzenesulfonamide], glibornuride [N-[[(3-hydroxy-4,7,7-trimethylbicyclo[2.2.1]hept-2-yl)amino]carbonyl]-4-methylbenzenesulfonamide], glisoxepid [N-[2-[4-[[[[(hexahydro-1H-azepin-1-yl)amino]carbonyl]amino]-sulfonyl]phenyl]ethyl]-5-methyl-3-isoxazolecarboxamide], glibenclamide [5-chloro-N-[2-[4-[[[(cyclohexylamino)carbonyl]-amino]sulfonyl]phenyl]ethyl]-2-methoxybenzamide], glisentide [N-[2-[4-[[[(cyclopentylamino)carbonyl] amino]sulfonyl]phenyl]-ethyl]-2-methoxybenzamide], glisolamide [N-[2-[4[[[(cyclohexyl-amino)carbonyl]amino] sulfonyl]phenyl]ethyl]-5-methyl-3-isoxazolecarboxamide], glybuzole [N-[5-(1,1-dimethylethyl)-1,3,4-thiadiazol-2-yl] benzenesulfonamide], glyclopyramide [4-chloro-N-[(1-pyrrolidinylamino)carbonyl]benzenesulfonamide] etc. as second generation sulfonylureas and pharmaceutically suitable acid addition salts thereof.

The most important biguanidine derivatives can be characterized by the formula

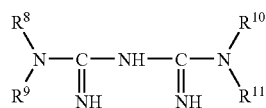

VI wherein
$R^8$, $R^9$, $R^{10}$ and $R^{11}$ represent, independently, a hydrogen atom, a $C_{1-10}$ alkyl group, a naphthyl group, a phenyl group or a phenyl($C_{1-4}$ alkyl) group, wherein in both former cases the phenyl group is optionally substituted by 1-3 substituents which can be, independently, a halo atom, a $C_{1-4}$ alkyl group or a $C_{1-4}$ alkoxy group, with the proviso that-one of $R^8$, $R^9$, $R^{10}$ and $R^{11}$ is other than a hydrogen atom, or
$R^8$ and $R^9$ together with the adjacent nitrogen atom and/or $R^{10}$ and $R^{11}$ together with the adjacent nitrogen atom form a 5- or 6-membered, saturated, unsaturated or aromatic ring that can be fused with a further 5- or 6-membered saturated, unsaturated or aromatic ring optionally containing also a nitrogen atom.

Especially preferred biguanidine derivatives are metformin [N,N-dimethylimidocarbonimidic diamide], buformin [N-butylimidodicarbonimidic diamide] and phenformin [N-(2-phenylethyl)imidodicarbonimidic diamide].

The α-glucosidase inhibitors inhibit the enzyme α-glucosidase. Important representatives thereof are, for example, miglitol [1,5-dideoxy-1,5-[(2-hydroxyethyl)imino]-D-glucitol], acarbose [O-4,6-dideoxy-4-[[[1S-(1α,4α,5β,6α)]-4,5,6-trihydroxy-(3-hydroxymethyl)-2-cyclohexen-1-yl] amino]-α-D-glucopyranosyl-(1→4)-O-α-D-glucopyranosyl-(1→4)-D-glucose], voglibose [3,4-dideoxy4-[[2-hydroxy-1-(hydroxymethyl)ethyl]amino]-2-C-(hydroxymethyl)-D-epiinositol] etc.

Under an anti-hyperlipidemic active agent any of the pharmacologically active agents conventionally used in the therapy for the treatment of high blood-lipid level is meant.

These are compounds that can be classified mainly as follows:
aryloxyalkanoic acid derivatives,
HMG coenzyme reductase inhibitors,
nicotinic acid derivatives,
antacids for bile acids.

Out of the aryloxyalkanoic acid derivatives, preferred active agents are e.g. clofibrate [2-(4-chlorophenoxy)-2-methyl-propanoic acid ethyl ester], gemfibrozil [5-(2,5-dimethyl-phenoxy) -2,2-dimethylpentanoic acid], simfibrate [2-(4-chloro-phenoxy) -2-methylpropanoic acid 1,3-propanediyl ester], etofibrate [3-pyridinecarboxylic acid 2-[2-(4-chlorophenoxy)-2-methyl -1-oxopropoxy]ethyl ester], ciprofibrate [2-[4-(2,2-dichlorocyclopropyl)phenoxy]-2-methylpropanoic acid], ronifibrate [3-pyridinecarboxylic acid 3-[2-(4-chlorophenoxy)-2-methyl -1-oxopropoxy]propyl ester] etc.

Out of the HMG coenzyme reductase inhibitors, the most important active agents are the following: lovastatin [[1 S-[1α (R*),3α,7β,8β(2S*,4S*),8αβ]]-2-methylbutanoic acid 1,2,3,7,8,8α-hexahydro-3,7-dimethyl-8-[2-(tetrahydro-4-hydroxy -6-oxo-2H-pyran-2-yl)ethyl]-1-naphthalenyl ester], fluvastatin [[R*,S*-(E)]-(±)-7-[3-(4-fluorophenyl)-1-(1-methyl-ethyl) -1H-indol-2-yl]-3,5-dihydroxy-6-heptenoic acid], pravastatin [[1S-[1α(βS*,δS*),2α,6α,8β(R*),8aα]]-1, 2,6,7,8,8a -hexahydro-β,δ,6-trihydroxy-2-methyl-8-(2-methyl-1-oxobutoxy)-1-naphthaleneheptanoic acid monosodium salt], simvastatin [[1S-[1α,3α,7β,8β(2S*,4S*),8αβ]]-2,2-dimethylbutanoic acid 1,2,3,7,8,8a-hexahydro-3,7-dimethyl-8-[2-(tetrahydro-4-hydroxy-6-oxo-2H-pyran-2-yl) ethyl]-1-naphthalenyl ester], atorvastatin [[R-(R*, R*)]-2-(4-fluorophenyl)-β,δ-dihydroxy-5-(1-methylethyl)-3-phenyl-4-[(phenylamino)carbonyl]-1H-pyrrole-1-heptanoic acid] etc.

Out of the nicotinic acid derivatives, for example, the following ones are used: acipimox [5-methylpyrazinecarboxylic acid 4-oxide], niceritrol [3-pyridinecarboxylic acid 2,2-bis [[(3-pyridinylcarbonyl)oxy]methyl]-1,3-propanediyl ester], nicomol [3-pyridinecarboxylic acid (2-hydroxy-1,3-cyclohexane-diylidene)-tetrakis(methylene) ester], nicoclonate [3-pyridine-carboxylic acid 1-(4-chlorophenyl)-2-methylpropyl ester] etc.

Out of the antacids that bind the bile acids, important ones are the following: colestipol [a basic anion exchange resin: N-(2-aminoethyl )-N'-[2-[(2-aminoethyl)amino]-ethyl]-1,2-ethane-diamine polymer with (chloromethyl)oxirane], cholestyramine [a synthetic, strongly basic anion exchange resin containing quaternary ammonium functional groups which are attached to a styrene-divinylbenzene copolymer], polidexide [an anion exchange resin containing quaternary ammonium groups which bind the bile acids in the intestine] etc.

The antidiabetic and anti-hyperlipidemic active agents are known from the literature. If desired and chemically possible, these active agents can be used in the form of the pharmaceutically suitable acid addition salts thereof or in the form of the salts formed with pharmaceutically suitable bases.

In the description and claims a $C_{1-4}$ alkyl group is a methyl, ethyl, n-propyl, isopropyl, n-butyl, sec.-butyl, tert.-butyl or isobutyl group.

A $C_{1-5}$ alkyl group may be, in addition to the ones listed above, e.g. an n-pentyl group, too.

A $C_{1-4}$ alkoxy group can be, for example, a methoxy, ethoxy, n-propoxy or n-butoxy group.

A halo atom is, for example, a fluoro, chloro, bromo or iodo atom.

A $C_{3-8}$ cycloalkyl group stands e.g. for a cyclopropyl, cyclo-pentyl, cyclohexyl, cycloheptyl or cyclooctyl group.

The 5- to 8-membered ring containing a nitrogen atom and which may contain a further heteroatom is, for example, a pyrrole, pyrazole, imidazole, oxazole, thiazole, pyridine, pyridazine, pyrimidine, piperazine, morpholine, indole, quinoline ring or the like.

A $C_{1-24}$ alkoxy group can be, in addition to the alkoxy groups listed above, e.g. also a n-pentoxy, decyloxy, dodecyloxy, octadecyloxy group etc.

A $C_{1-25}$ alkanoyl group is, for example, a formyl, acetyl, propionyl, butyryl, caproyl, palmitoyl, stearoyl group etc.

A $C_{3-9}$ alkenoyl group is e.g. an acryloyl, pentenoyl, hexenoyl, heptenoyl, octanoyl group etc.

When Y represents a group of the formula $R^7$—COO—, it can be, for example, a linolenoyl, linoloyl, docosahexaenoyl, eicosapentaenoyl, arachidonoyl group etc.

When $R^3$ stands for a pyridyl group, if desired, the nitrogen atom thereof may be in the form of the N-oxide. Similarly, when $R^1$ and $R^2$ form with the adjacent nitrogen atom a 5- to 8-membered ring, for example a piperidyl ring, if desired, the nitrogen atom thereof can be also present in the form of an N-oxide.

Under a pharmaceutically suitable acid addition salt, an acid addition salt formed with a pharmaceutically suitable inorganic acid such as hydrogen chloride or sulfuric acid and the like, or with a pharmaceutically suitable organic acid such as acetic acid, fumaric acid, lactic acid and the like is meant.

When the antidiabetic or anti-hyperlipidemic active agent has a chemical structure that can form a salt with a base, also the salt of the active agent formed with a pharmaceutically suitable inorganic or organic base can be used. When said active agent can form an acid addition salt with an acid, a pharmaceutically suitable acid addition salt of the active agent can be employed, too.

Within the hydroximic acid derivatives of the formula I, a preferred subclass consists of the hydroximic acid derivatives of the formula

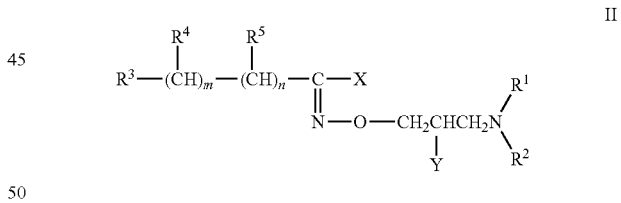

II wherein $R^1$, $R^2$, $R^3$, $R^4$, $R^5$, m and n are as defined for formula I, X stands for a halo atom or an amino group, Y represents a hydroxy group, and pharmaceutically suitable acid addition salts thereof.

The hydroximic acid derivatives of the formula II, wherein $R^1$ and $R^2$ form, together with the adjacent nitrogen atom, a piperidino group, $R^3$ is a pyridyl group, both m and n have a value of 0, X is as defined above, and pharmaceutically suitable acid addition salts thereof are particularly preferred. Out of them, O-(3-piperidino-2-hydroxy-1-propyl)nicotinic amidoxime and pharmaceutically suitable acid addition salts, particularly the monohydrochloride or dihydrochloride thereof are especially preferred.

Another advantageous subclass of the hydroximic acid derivatives of the formula I consists of the compounds of the formula

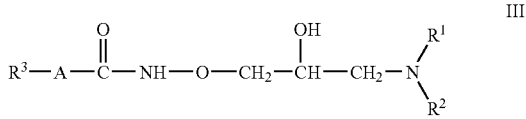

wherein $R^1$, $R^2$, $R^3$ and A are as defined for the formula I, and pharmaceutically suitable acid addition salts thereof.

A further preferred subclass of the hydroximic acid derivatives of the formula I consists of the cyclic compounds of the formula

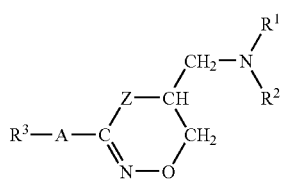

wherein $R^1$, $R^2$, $R^3$ and A are as defined for the formula I, Z represents an oxygen atom or a group of the formula —N= or —NH—, and pharmaceutically suitable acid addition salts thereof.

A still further preferred subclass of the hydroximic acid derivatives of the formula I consists of the compounds of the formula

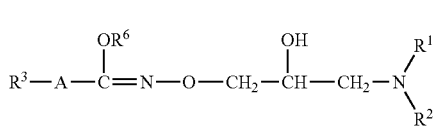

wherein $R^1$, $R^2$, $R^3$ and A are as defined for the formula I, $R^6$ stands for a $C_{1-4}$ alkyl group, and pharmaceutically suitable acid addition salts thereof.

The compounds of the formula I can be prepared by using processes known from U.S. Pat. No. 4,308,399, EP No. 417 210 and Hungarian patent application laid open under No. T/66350.

In the synergistic pharmaceutical combination of the invention the mass (or weight) ratio of (a) the antidiabetic or anti-hyperlipidemic active agent or, if desired and chemically possible, a pharmaceutically suitable acid addition salt or a salt formed with a pharmaceutically suitable base thereof and (b) the hydroximic acid derivative of the formula I or a pharmaceutically suitable acid addition salt thereof is, in general, (1-100):(100-1). The one or two pharmaceutical composition(s) of the pharmaceutical combination is/are suitable for peroral or parenteral administration and is/are solid or liquid composition(s). The suitable dosage forms and manufacture thereof as well as the useful carriers are known from the literature e.g. Remington's Pharmaceutical Sciences, Mack Publishing Co., Easton, USA.

Preferably, the synergistic pharmaceutical combination of the invention comprises (a) a hydroximic acid derivative of the formula II or a pharmaceutically suitable acid addition salt thereof and (b) an antidiabetic or anti-hyperlipidemic active agent or, if desired and chemically possible, a pharmaceutically suitable acid addition salt or a salt formed with a pharmaceutically suitable base thereof, wherein the active agents are present in separate pharmaceutical compositions or in a single common pharmaceutical composition. The antidiabetic or anti-hyperlipidemic active agent can be, for example, one of the species listed above. Thus, the preferred synergistic pharmaceutical combination of the invention may contain (a) a hydroximic acid derivative of the formula II e.g. O-(3-piperidino-2-hydroxy-1-propyl)nicotinic amidoxime or a pharmaceutically suitable acid addition salt thereof such as the dihydrochloride or monohydrochloride as well as ($b_1$) an antidiabetic active agent e.g. insulin, or an insulin sensitizing active agent such as a thiazolidinedione derivative, for example, pioglitazone, troglitazone, ciglitazone, rosiglitazone, or an active agent that enhance the production of insulin such as mitiglinide, repaglinide, senaglinide, or a sulfonamide such as tolbutamide, chlorpropamide, tolazamide, acetohexamide, glyburide, glipizide, gliclazide, glimepiride, gliquidone, glibornuride, glisoxepid, glibenclamide, glisentide, glisolamide, glybuzole, glyclopyramide, or a biguanidine derivative of the formula VI, preferably metformin, buformin, phenformin, or an α-glucosidase inhibitor such as miglitol, acarbose or voglibose, or ($b_2$) an anti-hyperlipidemic active agent e.g. an aryloxyalkanoic acid derivative such as clofibrate, gemfibrozil, simfibrate, etofibrate, ciprofibrate, ronifibrate, or a HMG coenzyme reductase inhibitor such as lovastatin, fluvastatin, pravastatin, simvastatin, atorvastatin, or a nicotinic acid derivative such as acipimox, niceritrol, nicomol, nicoclonate, or an antacid for bile acids such as colestipol, cholestyramine, polidexide, or, if desired and chemically possible, a pharmaceutically suitable acid addition salt or a salt formed with a pharmaceutically suitable base of the species given under ($b_1$) and ($b_2$).

Another preferred pharmaceutical combination of the invention comprises (a) a compound of the formula III, IV or V or a pharmaceutically suitable acid addition salt thereof, as well as ($b_1$) an antidiabetic active agent e.g. insulin, or an insulin sensitizing active agent such as a thiazolidinedione derivative, for example, pioglitazone, troglitazone, ciglitazone, rosiglitazone, or an active agent that enhance the production of insulin such as mitiglinide, repaglinide, senaglinide, or a sulfonamide such as tolbutamide, chlorpropamide, tolazamide, acetohexamide, glyburide, glipizide, gliclazide, glimepiride, gliquidone, glibornuride, glisoxepid, glibenclamide, glisentide, glisolamide, glybuzole, glyclopyramide, or a biguanidine derivative of the formula VI, preferably metformin, buformin, phenformin, or an α-glucosidase inhibitor such as miglitol, acarbose or voglibose, or ($b_2$) an anti-hyperlipidemic active agent e.g. an aryloxyalkanoic acid derivative such as clofibrate, gemfibrozil, simfibrate, etofibrate, ciprofibrate, ronifibrate, or a HMG coenzyme reductase inhibitor such as lovastatin, fluvastatin, pravastatin, simvastatin, atorvastatin, or a nicotinic acid derivative such as acipimox, niceritrol, nicomol, nicoclonate, or an antacid for bile acids such as colestipol, cholestyramine, polidexide, or, if desired and chemically possible, a pharmaceutically suitable acid addition salt or a salt formed with a pharmaceutically suitable base of the species given under ($b_1$) and ($b_2$).

The influence of the combination of the invention on the glucose sensitivity was studied using the following tests. All experiments performed conform to the European Community guiding principles for the care and use of experimental animals.

Adult male New Zealand white rabbits weighing 3-3.2 kg, housed in an animal room (12-hour light/dark periods a day, temperature of 22-25° C., relative humidity of 50-70%) with one animal per pen, fed commercial laboratory chow and tap water ad libitum, were used throughout. The animals underwent surgery after a two-week adaptation period.

Surgery was performed under aseptic conditions. The rabbits were anaesthetized with an intravenous bolus of 10 mg/kg diazepam (Sigma, St. Louis, Mo., USA) and 5 mg/kg ketamine (EGIS Pharmaceuticals Ltd., Budapest, Hungary). Lidocaine (EGIS Pharmaceuticals Ltd., Budapest, Hungary) was administered subcutaneously for local pain relief as described by Szilvassy Z. et al., Br. J. Pharmacol., 112, 999-1001 (1994). Polyethylene catheters were inserted into two major branches of the jugular vein and the left carotid artery. The catheters were exteriorised through the back of the neck. These lines were kept patent by filling with sodium heparin solution (100 IU/ml).

Hyperinsulinaemic Euglycaemic Glucose Clamp Studies

Human regular insulin was infused at a constant rate (13 mU/kg, NOVO Nordisk, Copenhagen) via one of the venous catheters over 120 min. This insulin infusion yielded plasma insulin immunoreactivity of 100±5 µU/ml in the steady state. This value corresponds to five times the value of the normal upper limit. Blood samples (0.3 ml) were taken from the arterial cannula for blood glucose concentration at 10 min intervals. Blood glucose concentration was maintained constant (5.5±0.5 mmol/liter) by a variable rate of glucose infusion via the second venous cannula. When blood glucose had stabilized for at least 30 min, we defined this condition as steady state. In the steady state, additional blood samples (0.5 ml) were taken for plasma insulin determination at 10-min intervals. The glucose infusion rate (mg/kg/min) during steady state was used to characterize insulin sensitivity [DeFronzo R.A. et al., Am. J. Of Physiol., 237, E214-223 (1979)]. The test compound(s) was/were administered to healthy and hypercholesterolaemic animals, respectively, perorally, in a single dose, daily, for five days, and the glucose infusion rates determined on the $6^{th}$ day were averaged within each test group consisting of 6 animals. One group of the healthy and one of the hypercholesterolaemic animals was used as the control. The results obtained are shown in Tables 1 and 2.

TABLE 1

Insulin sensitivity as characterized by the glucose infusion rate in mg/kg/min during steady state

| Group of animals | Control | BGP-15 30 mg/kg daily dose p.o. | Metformin 100 mg/kg daily dose p.o. | BGP-15 (30 mg/kg) + metformin (100 mg/kg) |
|---|---|---|---|---|
| normal | 14.6 ± 1.03 | 15.9 ± 1.82 | 15.8 ± 0.83 | 18.1 ± 0.92 |
| HC | 9.7 ± 1.0 | 13.4 ± 1.11 | 11.7 ± 0.87 | 15.8 ± 0.75 | normal = healthy animals were used in the test;
HC = hypercholesterolaemic animals were used in the test;
BGP-15 = O-(3-piperidino-2-hydroxy-1-propyl)nicotinic amidoxime hydrochloride.

TABLE 2

Insulin sensitivity as characterized by the glucose infusion rate in mg/kg/min during steady state

| Group of animals | Control | BGP-15 30 mg/kg daily dose p.o. | Troglitazone 75 mg/kg daily dose p.o. | BGP-15 (30 mg/kg) + troglitazone (75 mg/kg) |
|---|---|---|---|---|
| normal | 13.9 ± 1.22 | 15.4 ± 1.26 | 14.3 ± 0.08 | 16.9 ± 1.04 |
| HC | 9.0 ± 0.84 | 13.8 ± 1.29 | 14.1 ± 1.33 | 16.07 ± 0.84 | normal = healthy animals were used in the test;
HC = hypercholesterolaemic animals were used in the test;
BGP-15 = O-(3-piperidino-2-hydroxy-1-propyl)nicotinic amidoxime hydrochloride.

As a matter of fact, the amount of glucose infused to obtain constant blood glucose level has been measured in the above tests. It is favourable that a higher amount of glucose should be needed at the given constant blood glucose level which indicates the enhanced effect of insulin. Consequently, the higher glucose infusion rate is measured, the higher efficiency is obtained with the compound tested.

As seen in Table 1, in healthy animals, of course, higher values are obtained than in hypercholesterolaemic ones. In the control groups, lower glucose infusion rates are experienced than in the groups treated with either BGP-15 or metformin. Anyway, in both healthy and cholesterolaemic animals, the glucose infusion rates are significantly higher when the animals has been treated with both BGP-15 and metformin than in the case when only one of the test compounds has been administered. Thus, synergism is observed between BGP-15 and metformin.

The situation is the same with BGP-15 and troglitazone as shown by Table 2.

The invention includes also a method for the treatment or the prevention of a prediabetic state, metabolic X-syndrome or diabetes mellitus as well as disorders which are associated with the above states, namely, endogenic metabolic disorders, insulin resistance, dislipidemia and/or female endocrinic disorders based on androgenic preponderance, in which the patient suffering from or threatened by said states is treated with a therapeutically effective amount of, on the one hand, an antidiabetic or anti-lipidemic active agent, or, if desired and chemically possible, a pharmaceutically suitable acid addition salt or a salt formed with a pharmaceutically suitable base thereof, on the other hand, a hydroximic acid derivative of the formula I, or a pharmaceutically suitable acid addition salt thereof.

The antidiabetic or anti-hyperlipidemic active agent and the hydroximic acid derivative of the formula I can be administered simultaneously or one after the other following a shorter interval lasting for e.g. some seconds or minutes or a longer interval lasting for e.g. 10-30 minutes.

Since the hydroximic acid derivative of the formula I synergistically enhances the therapeutical effect of the antidiabetic or anti-hyperlipidemic active agent, in the process of the invention the daily dose of the antidiabetic or anti-hyperlipidemic agent is lower than the usual daily dose thereof employed in the conventional treatment when no hydroximic acid derivative of the formula I is administered.

Using the process of the invention, the development of especially the following clinical patterns can be prevented, or, when once developed, they can be influenced advantageously:

prediabetic state such as glucose intolerance or insulin resistance,
metabolic X-syndrome,
both types of diabetes (IDDM and NIDDM),
diabetic complications with special regards to retinopathy, neuropathy, nephropathy, polycystic ovary syndrome (PCOS), gestation diabetes mellitus (GDM), arterial hypertonia, dislipidemia, arteriosclerosis, obesitas, cardial ischemia associated with diabetes etc.

Thus, the invention includes the use of a hydroximic acid derivative of the formula I or a pharmaceutically suitable acid addition salt thereof for the preparation of a pharmaceutical composition which enhances synergistically the effect of an active agent, especially an antidiabetic or anti-hyperlipidemic active agent, employed for the prevention or treatment of a prediabetic state, metabolic X-syndrome or diabetes mellitus as well as disorders which are associated with the above states, namely endogenic metabolic disorders, insulin resistance, dislipidemia, alopecia, diffuse effluvium and/or female endocrinic disorders based on androgenic preponderance. Consequently, the pharmaceutical composition containing a hydroximic acid derivative of the formula I or a pharmaceutically suitable acid addition salt thereof as the active agent can be administered to a patient being treated with an antidiabetic or anti-hyper-lipidemic active agent in order to prevent or treat a prediabetic state, metabolic X-syndrome or diabetes mellitus as well as disorders which are associated with the above states, namely endogenic metabolic disorders, insulin resistance, dislipidemia, alopecia, diffuse effluvium and/or female endocrinic disorders based on androgenic preponderance. The administration of the pharmaceutical composition containing a hydroximic acid derivative of the formula I or a pharmaceutically suitable acid addition salt thereof as the active agent results in a lower dosage of the antidiabetic or anti-hyperlipidemic active agent. When a pharmaceutical composition containing a hydroximic acid derivative of the formula I or a pharmaceutically suitable acid addition salt thereof, for example, O-(3-piperidino-2-hydroxy-1-propyl) nicotinic amidoxime or a pharmaceutically suitable acid addition salt such as the dihydrochloride or the mono-hydrochloride thereof as the active agent is administered to a patient suffering from diabetes and obtaining a regular insulin treatment, then the daily insulin dose can be reduced, thus, avoiding the development of insulin resistance.

The invention claimed is:

1. A synergistic pharmaceutical combination for the treatment of a prediabetic state, metabolic X-syndrome, insulin sensitivity, glucose tolerance, dislipidemia or diabetes mellitus comprising:
   (a) a first pharmaceutical composition containing:
      insulin, and
      one or more conventional carrier(s), and
   (b) a second pharmaceutical composition containing O-(3-piperidino-2-hydroxy-1-propyl)nicotinic amidoxime or a pharmaceutically suitable acid addition salt thereof, and one or more conventional carrier(s).

2. A synergistic pharmaceutical combination for the treatment of a prediabetic state, metabolic X-syndrome, insulin sensitivity, glucose tolerance, dislipidemia or diabetes mellitus comprising:
   a single pharmaceutical composition comprising insulin and O-(3-piperidino-2-hydroxy-1-propyl) nicotinic amidoxime or a pharmaceutically suitable acid addition salt thereof, in addition to one or more conventional carrier(s).

3. A method for the treatment of a prediabetic state, metabolic X-syndrome, insulin sensitivity, glucose tolerance, dislipidemia or diabetes mellitus comprising
   administering the synergistic pharmaceutical combination according to claim 1 to a patient in need thereof.

4. A method for the treatment of a prediabetic state, metabolic X-syndrome, insulin sensitivity, glucose tolerance, dislipidemia or diabetes mellitus comprising:
   administering the synergistic pharmaceutical combination according to claim 2 to a patient in need thereof.

* * * * *